United States Patent [19]
Mori et al.

[11] Patent Number: 5,106,623
[45] Date of Patent: Apr. 21, 1992

[54] PEACH-LEAF EXTRACT AND BATH-ADDITIVE COMPOSITION COMPRISING THE SAME

[75] Inventors: Shinobu Mori, Kaminokawa; Hidenori Yorozu, Utsunomiya; Hirotaka Sato, Utsunomiya; Hakaru Inaoka, Utsunomiya; Yoshinori Nishizawa, Utsunomiya, all of Japan

[73] Assignee: Kao Corporation, Tokyo, Japan

[21] Appl. No.: 627,353

[22] Filed: Dec. 14, 1990

[30] Foreign Application Priority Data

Dec. 26, 1989 [JP] Japan .................................. 1-337226

[51] Int. Cl.$^5$ ............................................. A61K 35/78
[52] U.S. Cl. ................................................... 424/195.1
[58] Field of Search ..................................... 424/191.5

[56] References Cited

PUBLICATIONS

*Patent Abstracts of Japan*, Jun. 17, 1988, vol. 12, No. 213.
*Patent Abstracts of Japan*, Jan. 19, 1989, vol. 13, No. 24.
*Patent Abstracts of Japan*, Oct. 3, 1980, vol. 4, No. 140.

Primary Examiner—John W. Rollins
Attorney, Agent, or Firm—Oblon, Spivak, McClelland, Maier & Neustadt

[57] ABSTRACT

An extracted peach-leaf fraction, preparation method of the same and a bath-additive composition comprising the same is disclosed.

The extracted peach-leaf fraction is prepared by extracting peach-leaves with water and/or a lower alcohol, and treating the obtained extract with activated charcoal.

The peach-leaf fraction of the present invention has an excellent solubility and stability when dissolved in water, a high anti-inflammatory effect, and safety to the skin. Further, the bath-additive composition comprising the peach-leaf fraction has an excellent bathing effect without making the bath water turbid.

15 Claims, No Drawings

PEACH-LEAF EXTRACT AND BATH-ADDITIVE COMPOSITION COMPRISING THE SAME

BACKGROUND OF THE INVENTION

1. Field of the Invention

This invention relates to a specific fraction of peach leaves extracted from said leaves and treated with activated charcoal, and also relates to a bath-additive composition comprising said specific fraction of peach leaves.

2. Description of the Background Art

Conventionally, peach leaves have been used among people as a bath-additive since they are believed to be effective for curing miliaria and eczema. Agents for external application using extracts of peach leaves; for example, bath-additive compositions, creams, and the like, are known. Prior arts relating to such extracts of peach leaves were disclosed in Japanese Patent Laid-open (Kokai) No. 14,704/1988 (Title: Cosmetic composition comprising peach-leaf extract solution), Japanese Patent Laid-open (Kokai) No. 230,624/1988 (Title: Bath agent), and Japanese Patent Publication (Kokoku) No. 65,652/1988 (Title: Antibacterial and antimycotic agent).

At present, extracts of peach leaves are commercially sold as, for example, those concentrated at a temperature below 80° C. after heat-extraction or cold-extraction by water or aqueous ethanol, those prepared by mixing the above concentrated materials with concentrated glycerol, or the like. All these extracts are adjusted with solvents or made into soft extracts or dry powders to be used as components for cosmetic compositions or agents for external application such as bath-additive compositions, quasi-drugs, and the like.

However, the conventional peach-leaf extracts for external application have problems of the occurrence of precipitation and inferior safety. In addition, the effects of those agents for curing inflammatory diseases such as miliaria, eczema are not necessarily sufficient.

In this regard, there have been a desire to develop a peach-leaf fraction having good solubility and stability with water, and having no precipitation problem. It is also required to be effective on inflammatory diseases such as miliaria and safer to the living body, and further it must be produced economically in industry.

In view of this situation, the present inventors have undertaken extensive studies, and, as a result, found that the above problems could be solved by a peach-leaf fraction prepared by extracting peach leaves with water or a lower alcohol, or both and treating the extracts with activated charcoal. This finding has led to the completion of the present invention.

SUMMARY OF THE INVENTION

Accordingly, an object of this invention is to provide an extracted peach-leaf fraction prepared by extracting said fraction from peach-leaves with water and/or a lower alcohol, and treating said extract with activated charcoal.

Another object is to provide a bath-additive composition comprising said fraction of peach-leaves.

Other objects, features and advantages of the invention will hereinafter become more readily apparent from the following description.

DETAILED DESCRIPTION OF THE INVENTION AND PREFERRED EMBODIMENTS

Given as examples of the peach-leaves used in the present invention are those belonging to *Prunus persica* Batsch and *Prunus persica* Batsch var. davidi ana Maximowich. They can be served with or without stalks. Fresh leaves just collected or those air-dried after collection are preferred. The leaves are subjected to an extraction process preferably after cutting them into small pieces of less than 10 mm square in advance.

As extraction solvents, water and/or lower alcohols may be used. Examples of the lower alcohols are methanol, ethanol, n-propanol, isopropanol, n-butanol. They can be used as a mixture of two or more of them. Among the above solvents, water or ethanol, or their mixture is preferable, and ethanol mixed with 20-50% by weight of water is particularly preferable. For extraction, 6-12 parts by weight of the solvent may be added to one part by weight of raw material. There is no particular restriction as to extracting temperature, but preferable range is 50° -90° C. The extraction is generally performed under normal pressure, though it can be performed under a reduced pressure.

After filtration and/or concentration, the extract is subjected to treatment by means of activated charcoal. The activated charcoal may be a zootic charcoal, e.g., animal charcoal, born black, or a vegetable charcoal, e.g., coconut shell charcoal. Of these, the vegetable charcoal is most preferable because of its high adsorption capability and low cost. The amount of the activated charcoal to be used is 0.01-75% by weight and, preferably, 0.1-50% by weight, based on the amount of the raw peach-leaves. The treatment with the activated charcoal can be carried out in a batch system, with stirring by a mechanical means after the addition of the activated charcoal. The stirring is carried out, preferably, for from 15 minutes to 3 hours, and, most preferably, for from 30 minutes to 1 hour. After the treatment, the activated charcoal is removed by a suitable separating method such as filtration. The extract treated with the activated charcoal can be used as is without any additional treatments, or optionally be served as a soft extract after concentration or adjustment with a solvent. Further, the soft extract may be processed into a powder extract by drying: vacuum drying, freeze drying, spray drying, or the like.

The peach-leaf fraction thus obtained has excellent stability when dissolved in water, exhibits a good anti-inflammatory effect, and is safe to the skin. Moreover, since the extracted peach-leaf fraction of this invention can readily be concentrated and dried in production stages, it can be formulated into bath-additive compositions, cosmetic compositions, agents for external application, and the like.

For bath-additive compositions, the above-described peach-leaf fraction may be used independently or combined with other various components which are conventionally used as a component for bath-additive compositions. Examples of these components include inorganic salts such as sodium chloride, ammonium chloride, ammonium sulfate, aluminum sulfate, iron sulfate, sodium carbonate, sodium bicarbonate, calcium carbonate, magnesium carbonate, sodium hydrogencarbonate, calcium carbonate, magnesium carbonate, sodium sesquicarbonate, sulfur, sodium sulfide, potassium sulfide, sodium phosphate, sodium popophosphate, sodium thiophosphate, and the like; carbon dioxide or substances capable of releasing carbon dioxide; enzymes, emollient agents, humectants, oils, essential oils, galenicals, viscosity-increasing agents, surfactants, vitamins, alum, bacteriocides, reducing agents, perfumes, coloring substances, and the like.

Carbon dioxide may be incorporated in bath-additive compositions either by sealing carbon dioxide under a high pressure, or using substances containing carbon dioxide or substances capable of generating carbon dioxide. Preferable examples of the substances containing carbon dioxide are aluminosilicate and cyclodextrin or cyclodextrin derivatives. Any substances capable of generating carbon dioxide can be used insofar as they release carbon dioxide by chemical reaction. The combination of a carbonate and an acid is preferable. Examples of the carbonates used in this invention are sodium hydrogencarbonate, sodium sesquicarbonate, sodium carbonate, ammonium hydrogencarbonate, magnesium carbonate, and the like. As the acids, either organic or inorganic acids may be used, and those which are solid and soluble in water are desirable. Given as examples of the organic acids are dicarboxylic acids such as succinic acid, glutaric acid, adipic acid, fumaric acid, and the like; acidic amino acids such as glutamic acid, aspartic acid, and the like; oxyacids such as malic acid, citric acid, ascorbic acid, and the like; benzoic acid, pyrrolidone carboxylate, and their acidic salts, and the like. The inorganic acids are, for example, potassium dihydrogenphosphate, sodium sulfite, and the like.

The peach-leaf fraction of the present invention may be incorporated in these bath-additive components in a wide range of amount. When used as a powder extract, the amount to be incorporated is 0.1–20% by weight based on the total amount of the bath components, and when used as an extract or soft extract, a preferable amount is 0.3–65 g, converted to dried raw leaves, per single use.

The peach-leaf fraction of the present invention possesses excellent solubility and stability when dissolved in water, high anti-inflammatory effect, and safety to the skin. These characteristics are considered to be the effect of the activated-charcoal treatment in which active components are retained while water-insoluble components and allergic substances are removed from the peach-leaf extract. Accordingly, a bath-additive composition comprising the peach-leaf fraction of the present invention has an excellent bathing effect without making the bath water turbid.

Other features of the invention will become apparent in the course of the following description of the exemplary embodiments (Examples, Reference Examples and Experimental Examples) which are given for illustration of the invention and are not intended to be limiting thereof.

EXAMPLES

Example 1

Leaves of Chinese cultured peach after reaping the fruits were collected and air-dried. 10 kg of the dried leaves were cut into pieces of about 1 cm square and immersed in 80 l and then 50 l of 30% aqueous ethanol, each at a temperature of 80° C. for 2 hours, to prepare 100 l of an extract. To the extract was added 18 g of activated charcoal powder [Carboraffin: trade mark, manufactured by Takeda Chemical Industries, Ltd.) and the mixture was stirred at room temperature for 30 minutes. Thereafter, the activated charcoal was removed by filtration. The filtrate was concentrated under reduced pressure using an aspirator while heating at 40° C. in a warm bath for removing the solvent to obtain 1.79 Kg of an yellowish brown powder of the present invention.

EXAMPLE 2

Leaves of Chinese cultured peach after reaping the fruits were collected and air-dried. 10 kg of the dried leaves were cut into pieces of about 1 cm square and immersed in 80 l and then 50 l of 30% aqueous ethanol, each at a temperature of 80° C. for 2 hours, to prepare 100 l of an extract. To the extract was added 180 g of activated charcoal powder [Carboraffin: trade mark, manufactured by Takeda Chemical Industries, Ltd.) and the mixture was stirred at room temperature for 30 minutes. Thereafter, the activated charcoal was removed by filtration. The filtrate was concentrated under reduced pressure using an aspirator while heating at 40° C. in a warm bath for removing the solvent to obtain 1.79 Kg of an yellowish brown powder of the present invention.

Comparative Example 1

Leaves of Chinese cultured peach after reaping the fruits were collected and air-dried. 10 kg of the dried leaves were cut into pieces of about 1 cm square and immersed in 80 l and then 50 l of 30% aqueous ethanol, each at a temperature of 80° C. for 2 hours, to prepare 100 l of an extract. The extract was concentrated under reduced pressure using an aspirator while heating at 40° C. in a warm bath for removing the solvent to obtain 1.80 kg of an yellowish brown powder.

Comparative Example 2

10 kg of fresh peach-leaves were immersed in 120 l of 20% 1,3-butylene glycol aqueous solution at 25° C. for 10 days. The resultant extract was filtered and the filtrate was adjusted with 1,3-butylene glycol to obtain 130 kg of an extract.

Experimental Example 1

Carrageenin edema inhibitory test

1% carrageenin aqueous solution was subcutaneously administered to male mice (age: 4 weeks) at the sole of their legs. At intervals of two hours immediately after the administration, the sole was dipped at 35° C. for 30 minutes in a solution adjusted to have a concentration of extract equivalent to 1 g/10 l of peach leaves. The volume of a specified portion of the leg before and 4 hours, 6 hours after the administration of carrageenin was measured. One group consisted of 10 animals, and tap water was used as a control. An average edema-inhibitory ratio of each group was calculated and the results are shown in Table 1.

TABLE 1

| | Example | | Comparative Example (Unit: %) |
|---|---|---|---|
| | 1 | 2 | 1 |
| After 4 hours | 15.3 | 15.1 | 8.6 |
| (Evaluation) | − | − | − |
| After 6 hours | 23.6 | 23.8 | 23.3 |
| (Evaluation) | + | + | + |

Evaluation standard:
−: Inhibitory ratio is less than 20%
+: Inhibitory ratio is greater than 20%

Experimental Example 2

UV-light erythema inhibitory test

A sample liquid adjusted to have a concentration of extract equivalent to 1 g/10 ml of peach leaves was prepared UV-light (0.8 mW/cm$^2$) was irradiated onto four clipped and shaved areas (2 cm×2 cm) on lateral region of guinea pigs for 9 minutes. Immediately after the irradiation, the clipped and shaved areas were dipped in the sample liquid at 37° C. for 30 minutes. Tap water was used as a control. The condition of erythema was observed 24 hours after the irradiation of UV-light and scored according to the following standard. The total score of the four areas was defined as a score of an individual. One group consisted of 10 individuals, and tap water was used as a control. Under these conditions, difference in the average score of each group from that of the control group was calculated. The results are shown in Table 2.

Evaluation point 0: no reaction
point 0.5: slight or disseminated erythema was observed
point 1: clear erythema was observed

TABLE 2

|  | (Unit: difference in the score of each group from that of the control group) | | | |
|---|---|---|---|---|
|  | Example | | Comparative Example | |
|  | 1 | 2 | 1 | 2 |
| Erythema inhibition | 0.65 | 0.65 | 0.50 | 0.16 |
| (Evaluation) | + | + | + | − |

Evaluation standard:
−: The difference in the score from the score of the control group is less than 0.5 (Inhibiting rate: less than 20%)
+: The difference in the score from the score of the control group is greater than 0.5 (Inhibiting rate: greater than 20%)

As clearly shown in Experimental Examples 1 and 2, the peach-leaf fraction of the present invention was confirmed to have an anti-inflammatory effect equivalent to or higher than that of Comparative Examples 1 and 2.

Experimental Example 3

Precipitation test

Each fraction obtained in Examples 1, 2 and Comparative Examples 1, 2 was taken in an amount equivalent to 15 g and 30 g of raw leaves, and dissolved in 50 ml of water at 40° C. The mixed solution was allowed to stand in a cold storage at 5° C. for one hour. Thereafter, 10 ml of the solution was collected in a Spit centrifugal tube, and centrifuged at 3,000 rpm for 10 minutes. The amount of precipitate thus obtained was measured. As a sample of Comparative Example 2, the neat liquid containing 1,3-butylene glycol was used. The results are shown in Table 3.

TABLE 3

|  |  |  |  | (Unit: ml) |
|---|---|---|---|---|
|  | Example | | Comparative Example | |
|  | 1 | 2 | 1 | 2 |
| Concentration (leaves g/50 ml) |  |  |  |  |
| 15 | <0.02 | <0.02 | 0.02 | <0.02 |
| (Evaluation) | AAA | AAA | BBB | AAA |
| 30 | <0.02 | <0.02 | 0.08 | <0.02 |
| (Evaluation) | AAA | AAA | CCC | AAA |

Evaluation standard:
AAA: the amount of precipitate is less than 0.02 ml
BBB: the amount of precipitate is greater than 0.02 ml and less than 0.05 ml
CCC: the amount of precipitate is greater than 0.05 ml

Experimental Example 4

Dissolution test by turbidity

Each fraction obtained in Examples 1, 2 and Comparative Examples 1, 2 was taken in an amount equivalent to 0.3 g of leaves, and dissolved in 50 ml of water at 40° C. The turbidity of each solution immediately after the dissolution and after one hour cold storage at 5° C. was measured by means of a turbidimeter (Voic integrating sphere turbidimeter). The neat liquid containing 1,3-butylene glycol was used as the sample for Comparative Example 2. The results are shown in Table 4.

TABLE 4

|  |  |  |  | (Unit: ppm) |
|---|---|---|---|---|
|  | Example | | Comparative Example | |
|  | 1 | 2 | 1 | 2 |
| Before cold-storage | 7.7 | 4.0 | 19.8 | 13.5 |
| (Evaluation) | AAA | AAA | CCC | BBB |
| After cold-storage | 3.7 | 2.8 | 18.8 | 18.3 |
| (Evaluation) | AAA | AAA | CCC | CCC |

Evaluation standard:
AAA: a degree of turbidity is less than 10 ppm
BBB: a degree of turbidity is greater than 10 ppm and less than 15 ppm
CCC: a degree of turbidity is greater than 15 ppm From Experimental Examples 3 and 4, the peach-leaf fraction of this invention was confirmed to have an excellent solubility and stability against water.

Experimental Example 5

Cutaneous sensitization test (CCET method)

A 20% aqueous solution of the peach fraction obtained in Example 1 was close-patched on the lateral region of guinea pigs on the first, second, seventh and ninth day, and Freund's adjuvant was administered to sensitize them on the seventh day. On the 21st day, each 20% aqueous solution of the fraction obtained in Comparative Example 1 and Examples 1, 2 was applied to the lateral region of guinea pigs to elicit. The condition of cutaneous eczematization was inspected 24 hours, 48 hours, and 72 hours after the application. Distilled water was used as a control. One group consisted of 10 individuals. The results are shown in Table 5.

TABLE 5

|  | (Unit: population having positive allergic eczema) | | |
|---|---|---|---|
|  | Example | | Comparative Example |
|  | 1 | 2 | 1 |
| After 24 hours | 0 | 0 | 0 |
| (Evaluation) | AAA | AAA | AAA |
| After 48 hours | 0 | 0 | 1 |
| (Evaluation) | AAA | AAA | BBB |
| After 72 hours | 0 | 0 | 2 |
| (Evaluation) | AAA | AAA | BBB |

Evaluation standard:
AAA: all individuals are negative
BBB: at least one individual is positive The above results clearly showed that the fractions obtained in Examples 1, 2 had no action of cutaneous sensitization which was observed on the sample obtained in Comparative Example. Further, the peach-leaf fraction of the present invention was confirmed to have high safety to the living body in such a harsh test.

Any peach-leaf fractions obtained in Examples and Comparative Example showed no cutaneous stimulus action.

Table 6 summarizes the aforementioned five test results, showing that the peach-leaf fraction of the present invention satisfies all functions of anti-inflammatory effect, excellent solubility and stability when dissolved in water, and safety to the skin.

TABLE 6

|  | Example | | Comparative Example | |
|---|---|---|---|---|
|  | 1 | 2 | 1 | 2 |
| Carrageenin edema inhibitory test | Good | Good | Good | — |
| UV-light erythema inhibitory test | Good | Good | Good | Bad |
| Precipitation test | Good | Good | Bad | Bad |
| Turbidity test | Good | Good | Bad | Bad |
| Cutaneous sensitization test | Good | Good | Bad | — |
| Comprehensive evaluation | Good | Good | Bad | Bad |

EXAMPLE 3

3 g of the peach-leaf fraction prepared in Example 1, 26.8 g of sodium bicarbonate, 0.1 g of perfume, and 0.1 g of pigment were mixed in this order to produce a bath powder weighing 30 g for single use.

EXAMPLE 4

3 g of the peach-leaf fraction prepared in Example 2, 25.9 g of sodium bicarbonate, 20.9 g of succinic acid, 0.1 g of perfume, 0.1 g of pigment were mixed in this order to produce a bath tablet weighing 50 g per one tablet.

Comparative Example 3

3 g of the peach-leaf extract prepared in Comparative Example 1, 26.8 g of sodium bicarbonate, 0.1 g of perfume, and 0.1 g of pigment were mixed in this order to produce a bath powder weighing 30 g for single use.

Comparative Example 4

3 g of the peach-leaf extract prepared in Comparative Example 1, 25.9 g of sodium bicarbonate, 20.9 g of succinic acid, 0.1 g of perfume, 0.1 g of pigment were mixed in this order to produce a bath tablet weighing 50 g per one tablet.

Experimental Example 6

The bath-additive compositions prepared in the above Examples 3, 4 and Comparative Examples 3, 4 were each dissolved in 200 l of bath water. The bathing effects of these bath-additive compositions were evaluated by 30 panelists for ten days according to a conventional mode. The overall evaluation (comprehensive feeling upon use), moisturized feeling to the skin, warming effect to the body, and turbidity of the water on the following day were recorded and summarized in Table 7.

TABLE 7

| Comparison | Evaluation Items | Evaluation* | | |
|---|---|---|---|---|
|  |  | AAA | BBB | CCC |
| Comparison between | Overall | 17 | 6 | 7 |
| Example 3 and | evaluation | | | |
| Comparative Example 3 | Warming effect | 13 | 10 | 7 |
|  | Moisturized feeling | 14 | 8 | 8 |
|  | Turbidity on the following day | 19 | 6 | 5 |
| Comparison between | Overall | 18 | 6 | 6 |
| Example 4 and | evaluation | | | |
| Comparative Example 4 | Warming effect | 12 | 10 | 8 |
|  | Moisturized feeling | 12 | 9 | 9 |
|  | Turbidity on the following day | 21 | 6 | 3 |

*Each figure shows the number of panelists who gives the following evaluation.
AAA: Bath-additive prepared from Example is better
BBB: Can not tell which is better
CCC: Bath-additive prepared from Comparative Example is better As evidenced in the above results, the bath-additive composition of the present invention has superiority to the Comparative Examples or conventional bath-additive compositions in all of these evaluation items.

Obviously, numerous modifications and variations of the present invention are possible in light of the above teachings. It is therefore to be understood that within the scope of the appended claims, the invention may be practiced otherwise than as specifically described herein.

What is claimed is:

1. A peach-leaf fraction prepared by a process comprising the steps of:
   extracting peach-leaves with water or a lower alcohol or both, and
   contacting the obtained extract with activated charcoal to obtain said peach-leaf fraction.

2. A bath-additive composition comprising the peach-leaf fraction according to claim 1, and other ingredients commonly accepted for bath-additive composition.

3. The composition of claim 2, comprising 0.1–20 wt. % of said peach-leaf fraction.

4. The composition of claim 2, further comprising an inorganic salt.

5. The composition of claim 2, further comprising carbon dioxide or a substance capable of releasing carbon dioxide.

6. The composition of claim 2, further comprising a component selected from the group consisting of enzymes, emollient agents, humectants, oils, essential oils, galenicals, viscosity-increasing agents, surfactants, vitamins, alum, bacteriacides, reducing agents, perfumes and coloring substances.

7. The composition of claim 2, further comprising a mixture of a carbonate and an acid.

8. A process of preparing a peach-leaf fraction, comprising the steps of:
   extracting peach leaves with water, a lower alcohol or mixtures thereof, and
   contacting the obtained extract with activated charcoal to obtain said peach leaf fraction.

9. The process of claim 8, wherein said lower alcohol is selected from the group consisting of methanol, ethanol, n-propanol, isopropanol and n-butanol.

10. The process of claim 8, wherein said extracting step is conducted using a mixture of ethanol with 20–50% by weight water.

11. The process of claim 8, wherein said extracting step is conducted using 6–12 parts by weight of said water, lower alcohol or mixture to 1 part by weight of said peach leaves.

12. The process of claim 8, wherein said contacting step is conducted using 0.01-75% by weight activated charcoal based on the amount of said peach leaves.

13. The process of claim 8, wherein said contacting step is conducted using 0.1-50% by weight activated charcoal based on the amount of said peach leaves.

14. The process of claim 8, further comprising removing said water, lower alcohol or mixture to obtain a powder.

15. The process of claim 14, wherein said solvent is removed by vacuum drying, freeze drying or spray drying.

* * * * *